(12) United States Patent
Sholev

(10) Patent No.: US 11,134,973 B2
(45) Date of Patent: Oct. 5, 2021

(54) ADAPTOR OR ADAPTOR SYSTEM FOR RENDERING MEDICAL DEVICES FUNCTIONALLY STERILE

(71) Applicant: Human Xtensions Ltd., Netanya (IL)

(72) Inventor: Mordehai Sholev, Moshav Amikam (IL)

(73) Assignee: Human Xtensions Ltd., Netanya (IL)

( * ) Notice: Subject to any disclaimer, the term of this patent is extended or adjusted under 35 U.S.C. 154(b) by 75 days.

(21) Appl. No.: 16/660,943

(22) Filed: Oct. 23, 2019

(65) Prior Publication Data

US 2020/0054354 A1 Feb. 20, 2020

Related U.S. Application Data

(63) Continuation of application No. 15/735,211, filed as application No. PCT/IL2016/050621 on Jun. 14, 2016, now Pat. No. 10,492,813.

(Continued)

(51) Int. Cl.
*A61B 17/32* (2006.01)
*A61L 2/26* (2006.01)
(Continued)

(52) U.S. Cl.
CPC ........ *A61B 17/32* (2013.01); *A61B 17/00234* (2013.01); *A61B 17/1622* (2013.01); *A61B 46/10* (2016.02); *A61B 90/08* (2016.02); *A61B 90/90* (2016.02); *A61L 2/26* (2013.01); *A61B 90/98* (2016.02); *A61B 2017/0046* (2013.01); *A61B 2017/00398* (2013.01);
(Continued)

(58) Field of Classification Search
CPC ....... A61B 17/00; A61B 17/16; A61B 17/162; A61B 17/1624; A61B 17/1626; A61B 17/1628; A61B 17/1631; A61B 17/1642; A61B 17/1633; E21B 17/02; E21B 17/07
See application file for complete search history.

(56) References Cited

U.S. PATENT DOCUMENTS 5,599,093 A 2/1997 Hoftman et al.
5,993,454 A 11/1999 Longo
(Continued)

FOREIGN PATENT DOCUMENTS

CN 102630154 8/2012
CN 102892374 1/2013
(Continued)

OTHER PUBLICATIONS

International Preliminary Report on Patentability dated Dec. 28, 2017 From the International Bureau of WIPO Re. Application No. PCT/IL2016/050621. (8 Pages).
(Continued)

*Primary Examiner* — Daniel J Wiley

(57) ABSTRACT

An adaptor for coupling a surgical tool to a handle having a drive mechanism for operating the surgical tool is provided. The adaptor includes two telescopically connected segments, a first segment being for engaging the surgical tool and a second segment for engaging the handle. When the first and the second segments are telescopically collapsed they operatively link the surgical tool with the handle drive mechanism while preventing user contact with potentially non-sterile regions of the handle and/or tool.

6 Claims, 16 Drawing Sheets

Related U.S. Application Data

(60) Provisional application No. 62/175,491, filed on Jun. 15, 2015.

(51) Int. Cl.
  *A61B 46/10* (2016.01)
  *A61B 17/16* (2006.01)
  *A61B 17/00* (2006.01)
  *A61B 90/00* (2016.01)
  *A61B 90/90* (2016.01)
  *A61B 90/98* (2016.01)

(52) U.S. Cl.
  CPC .............. *A61B 2017/00455* (2013.01); *A61B 2017/00477* (2013.01); *A61B 2017/00486* (2013.01); *A61B 2017/00991* (2013.01); *A61B 2090/0803* (2016.02); *A61L 2202/24* (2013.01)

(56) References Cited

U.S. PATENT DOCUMENTS

| | | | |
|---|---|---|---|
| 6,847,190 | B2 | 1/2005 | Schaefer et al. |
| 7,622,892 | B2 | 11/2009 | Kim et al. |
| 8,105,338 | B2 | 1/2012 | Anderson et al. |
| 8,278,873 | B2 | 10/2012 | Smith et al. |
| RE44,713 | E | 1/2014 | Jung |
| 2002/0095177 | A1 | 7/2002 | Kupferschmid et al. |
| 2002/0171208 | A1 | 11/2002 | Lechot et al. |
| 2004/0267297 | A1 | 12/2004 | Malackowski |
| 2011/0057609 | A1 | 3/2011 | Smith et al. |
| 2011/0277775 | A1 | 11/2011 | Holop et al. |
| 2012/0112690 | A1 | 5/2012 | Stulen et al. |
| 2012/0116380 | A1 | 5/2012 | Madan et al. |
| 2013/0340238 | A1* | 12/2013 | Shores ................. A61B 17/162 29/525.01 |
| 2014/0262408 | A1 | 9/2014 | Woodard |
| 2018/0168675 | A1 | 6/2018 | Sholev |

FOREIGN PATENT DOCUMENTS

| | | |
|---|---|---|
| EP | 2210565 | 7/2012 |
| EP | 2684530 | 1/2014 |
| JP | 2008-104854 | 5/2008 |
| JP | 2013-526337 | 6/2013 |
| WO | WO 2016/203466 | 12/2016 |

OTHER PUBLICATIONS

International Search Report and the Written Opinion dated Oct. 21, 2016 From the International Searching Authority Re. Application No. PCT/IL2016/050621.

Notification of Office Action and Search Report dated Sep. 4, 2019 From the State Intellectual Property Office of the People's Republic of China Re. Application No. 201680032792.8. (8 Pages).

Official Action dated Mar. 5, 2019 From the U.S. Appl. No. 15/735,211. (13 Pages).

Supplementary European Search Report and the European Search Opinion dated Jan. 7, 2019 From the European Patent Office Re. Application No. 16811134.2. (12 Pages).

Translation Dated Sep. 18, 2019 of Notification of Office Action dated Sep. 4, 2019 From the State Intellectual Property Office of the People's Republic of China Re. Application No. 201680032792.8. (10 Pages).

Alcobra Metals "Aluminum Telescoping Tube 6005A-T6 Telescoping Round Tube", Alcobra Metals, Inc., XP055536045, Retrieved From the Internet, 6 P., Feb. 16, 2015.

Office Action dated Dec. 30, 2020 From the Israel Patent Office Re. Application No. 256262. (3 Pages).

Notification of Office Action dated Feb. 3, 2020 From the State Intellectual Property Office of the People's Republic of China Re. Application No. 201680032792.8 and Its Translation Into English. (17 Pages).

Notice of Reasons for Rejection dated Mar. 24, 2020 From the Japan Patent Office Re. Application No. 2017-561870 and Its Translation Into English. (10 Pages).

Search Report and Explanations dated May 28, 2020 From ther Servico Publico Federal, Ministerio da Economia, Instituto Nacional da Propriedade Industrial do Brasil Re. Application No. BR112017026803-5 and Its Translation Into English. (6 Pages).

Summons to Attend Oral Proceedings Pursuant to Rule 115(1) EPC dated Feb. 4, 2021 From the European Patent Office Re. Application No. 16811134.2. (6 Pages).

Communication Pursuant to Article 94(3) EPC dated Apr. 14, 2020 From the European Patent Office Re. Application No. 16811134.2. (4 Pages)

Examination Report dated Feb. 20, 2020 From the Australian Government, IP Australia Re. Application No. 2016279033. (3 Pages).

Examination Report Under Sections 12 & 13 of the Patents Act, 1970 and the Patents Rules, 2003 dated Mar. 12, 2021 From the Government of India, Intellectual Property India, Patents, Designs, Trade Marks, Geographical Indications, The Patent Office Re. Application No. 201727042250. (5 Pages).

* cited by examiner

US 11,134,973 B2

ADAPTOR OR ADAPTOR SYSTEM FOR RENDERING MEDICAL DEVICES FUNCTIONALLY STERILE

RELATED APPLICATIONS

This application is a continuation of U.S. patent application Ser. No. 15/735,211, filed on Dec. 11, 2017, which is a National Phase of PCT Patent Application No. PCT/IL2016/050621 having International filing date of Jun. 14, 2016, which claims the benefit of priority under 35 USC § 119(e) of U.S. Provisional Patent Application No. 62/175,491 filed on Jun. 15, 2015. The contents of the above applications are all incorporated by reference as if fully set forth herein in their entirety.

FIELD AND BACKGROUND OF THE INVENTION

The present invention relates to an adaptor or adaptor system that can be used to render medical devices functionally sterile thus enabling repeated use thereof without having to subject such devices to sterilization.

Devices that utilize electrical motors and components are well known in the art of medicine. Such devices and especially electrical components thereof can be difficult to sterilize due to their complexity and sensitivity to sterilizing agents or conditions. Although some motorized/electrical devices can be sterilized using known sterilization processes, exposure of such devices to repeated sterilization increases the risk of damaging electrical and mechanical components. Since such devices must be sterilized prior to each use, the number of procedures that can be performed using such a device may be limited by the number of sterilization cycles it can survive. In addition, the mechanical design of a device suitable for sterilization requires sealing that may be bulky, expensive and complicated.

There is thus a need for an approach that can render non-sterile devices components functionally sterile without having to subject such devices to sterilization.

SUMMARY OF THE INVENTION

The present invention successfully addresses the shortcomings of the presently known configurations by providing a device for rendering non-sterile medical device components functionally sterile while enabling coupling of sterile and non-sterile device components.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE SEVERAL VIEWS OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 6a-10 illustrate an adaptor system constructed in accordance with the teachings of the present invention.

FIGS. 6a-b show the handle with and without cap (respectively).

FIG. 7 shows the handle and surgical tool components of the present adaptor system.

FIG. 9 shows the contraction of the external cover, while the tool gears housing is connected to the driving handle.

FIG. 10 is a cut-away view showing the tool connected to the handle drive mechanism.

DESCRIPTION OF THE PREFERRED EMBODIMENTS

Figure 1:
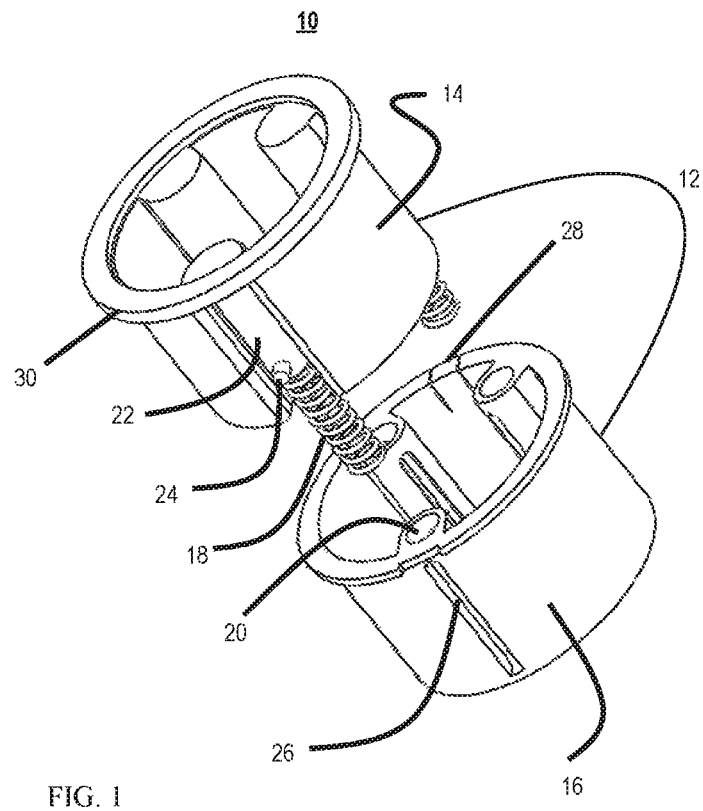
FIG. 1 is an exploded view of the components of the present adaptor.

The present invention is of an adaptor which can be used to render non-sterile medical devices functionally sterile. Specifically, the present invention can be used to prevent user contact with potentially non-sterile regions of medical devices that include motors and electrical/mechanical components thus rendering such devices functionally sterile.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The problem of repeatedly sterilizing complex medical devices that include mechanical and/or electrical components is well known in the art. While reducing the present invention to practice, the present inventor devised a solution to such problem by providing an adaptor that can cover potentially non-sterile regions of electrical/mechanical device portions (e.g. device handle including a drive mechanism) while providing an interface to sterile and disposable components that are attachable to such electrical/mechanical device portions. Thus, the present invention enables use of a device that includes non-sterile components under sterile conditions.

As is further described herein, the present invention includes an adaptor that enables coupling of a non-sterile device portion (e.g. motorized handle) to a sterile portion (e.g. laparoscopic shaft) allowing the surgeon to work safely with the two connected device portions without being contaminated by the non-sterile portion. In addition, the present adaptor enables the surgeon to disconnect the drive handle from the laparoscopic shaft without being exposed to non-sterile regions of the device and reuse the tool and handle any number of times in the same procedure without fear of contaminating the staff or the environment.

Thus, according to one aspect of the present invention, there is provided a device for coupling a surgical tool to a handle having a drive mechanism for operating the surgical tool. Examples of a surgical tool include an endoscope/laparoscope shaft, a grasper or a mono polar hook or tool with bi-polar jaws with cutting element. The surgical tool can be a simple straight grasper or cutter, or it can include a deflectable shaft. The handle can be a control handle provided with a manual or motorized drive mechanism and related interface as well as other components for interfacing with external devices (e.g. fluid source, monitors, diathermia control device or any other computerized devices). In general, the surgical tool portion is operated inside the body while the handle portion is operated outside the body.

In one embodiment, the present device (also referred to herein as an "adaptor") includes two telescopically connected segments. The first segment is configured for engaging the surgical tool and the second segment is configured for engaging the handle. When the first and second segments are telescopically collapsed (one inside the other) they operatively enable the connection between the surgical tool and the handle drive mechanism.

In addition, when collapsed the segments form a cover around the non-sterile region coupling the handle to the surgical tool, i.e. the handle portion which is non-sterile is internalized within the adaptor and although the handle drive mechanism can be in direct contact with the shaft of the surgical tool, it is not exposed to the operator or environment and there is thus no fear of contamination to the environment or operator. Furthermore, disengaging the shaft from the handle leaves potentially contaminated or contaminable portions of the surgical tool covered thus protecting the user and environment from contact with potentially contaminated regions of the surgical tool.

In another embodiment of the present invention two adaptors are used for functional sterilization, a first adaptor connected to handle and a second adaptor connected to the surgical tool.

Thus, the present invention enables use of non-sterile components without fear of contaminating the environment or user.

Referring now to the drawings, FIGS. 1-5c illustrate an embodiment of the present device which is referred to herein as adaptor 10.

Adaptor 10 includes two telescopically collapsible segments 12, a first (tool) segment 14 which can be coupled to a surgical tool, and a second (handle) segment 16 which can be coupled to a handle.

FIG. 1 is an exploded view of adaptor 10 showing the relationship between segments 14 and 16. Segment 14 includes one or more springs 18 (three shown) for enabling compression of segment 14 into segment 16 against a spring force. Spring(s) 18 facilitate automatic telescopic opening of segments 14 and 16 when collapsed in a closed (operative) position. Segment 14 also includes rods 22 fitted with pins 24 for guiding telescopic movement of segments 14 and 16 through assembling and disassembling cycles. Spring(s) 18 and rods 22 fit into holes 20 in segment 16. Pins 24 fit into guide grooves 26 in segment 16.

Segments 14 and 16 also include circumferential protrusions 28 and 30 (respectively). Protrusion 28 locks segment 16 to the opening of the electromechanical device to ensure that segment 16 will not move with respect to the covered non-sterile region. Protrusion 30 ensures the correct orientation between segments 14 and 16 to ensure that protrusion 28 will be at the right locking position.

Figure 2:
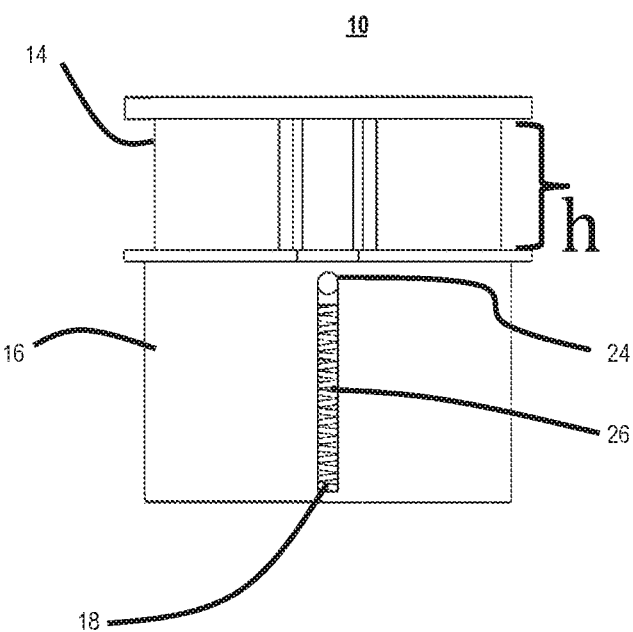
FIG. 2 is a side view of the assembled adaptor of FIG. 1.
Figure 3:
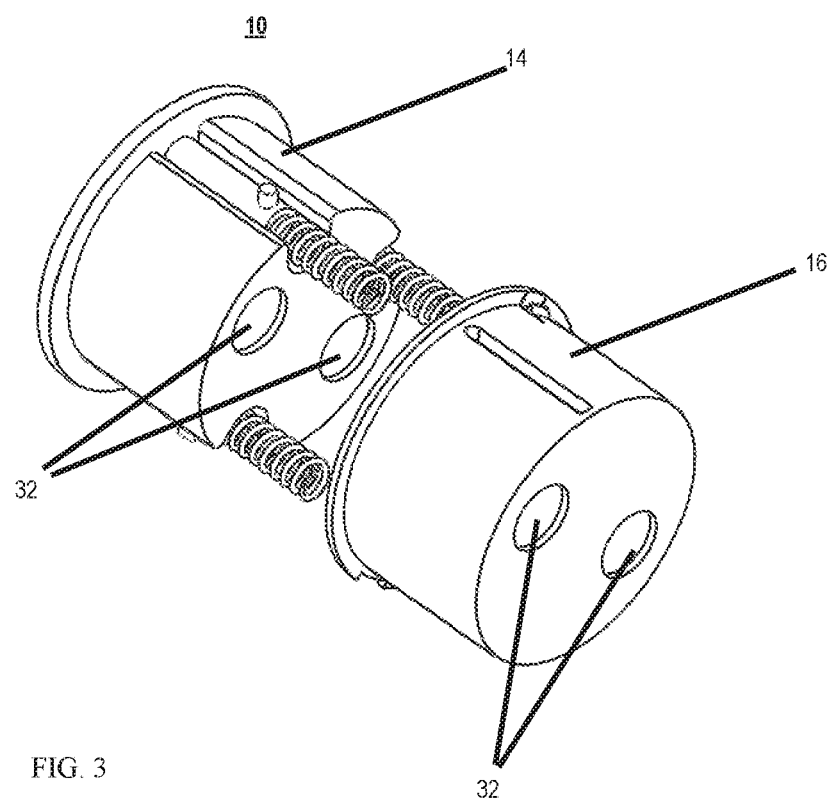
FIG. 3 is an isometric view of the present adaptor showing the drive shaft access holes in both segments of the adaptor.

The assembled adaptor 10 is shown in side view in FIG. 2. The open (non-operative) distance between bottom of segment 14 and the bottom of segment 16 is indicated by 'h'.

Segments 14 and 16 can be fabricated from a polymer or alloy or any material that can be sterilized via autoclave or another sterilization approach. Segments 14 and 16 can be shaped as cylinders or any other shape suitable for functionality. Segments 14 and 16 can each be 10-60 mm in diameter (D) and 10-40 mm in height (H). The distance between protrusion 28 and protrusion 30 can be 10-40 mm, when adaptor is open. When closed, bottom of segment 14 and the bottom of segment 16 may be typically in contact with each other.

Segments 14 and 16 can be each coupled to the tool and handle (respectively) using couplers such as protrusion 28 of part 16 that fits a groove in the opening of the electromechanical device which locks segment 14 to the opening of the electromechanical device to ensure that segment 14 will not move with respect to the covered non-sterile region.

Figures 4A, 4B:
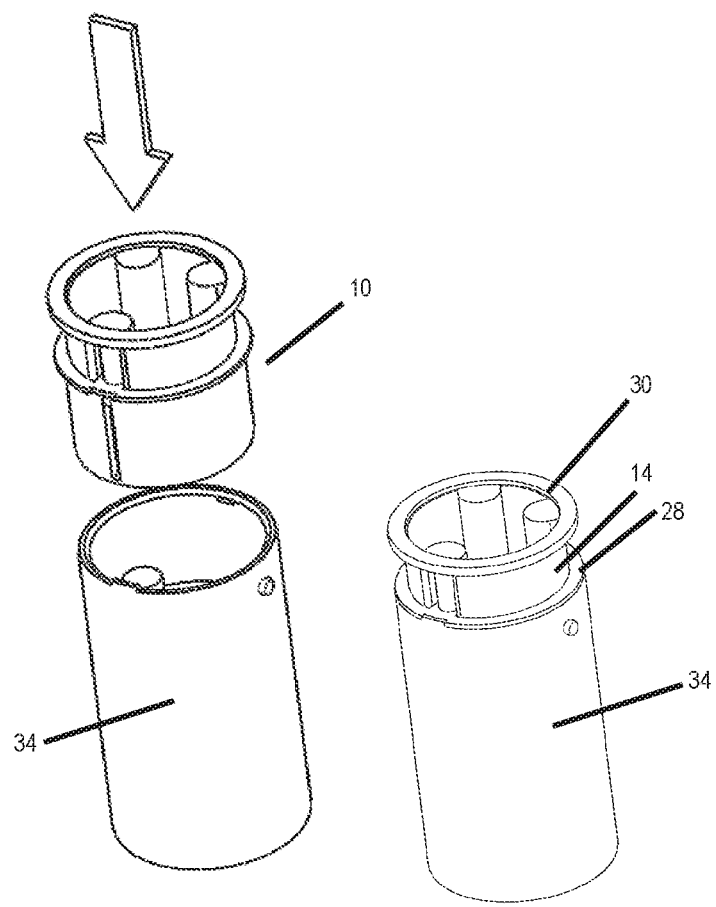
FIGS. 4a-b illustrate coupling of the present adaptor to a drive mechanism portion of a handle.

FIGS. 4a-b illustrate coupling of adaptor 10 (in the open, non-collapsed state) to a handle (electro mechanical device). For the sake of simplicity and clarity, only the drive portion of the handle is shown. Segment 16 is coupled to drive mechanism 34 without collapsing segment 14 into segment 16. This protects the inner part of drive mechanism 34 of the handle from exposure to the environment. Once drive mechanism 34 is connected to segment 16, a surgical tool 36 (e.g. laparoscopic grasper) is fitted into segment 14 and segments 14 and 16 are compressed (collapsed) to couple drive mechanism 34 to gear house 43 of shaft 38 of surgical tool 36 through holes 32, shown in FIG. 3. Cap 40 is fitted over shaft 38 of surgical tool 36 and then used to lock (using screw cap with lock pin) segments 14 and 16 in a compressed (operative) state.

Figure 5A:
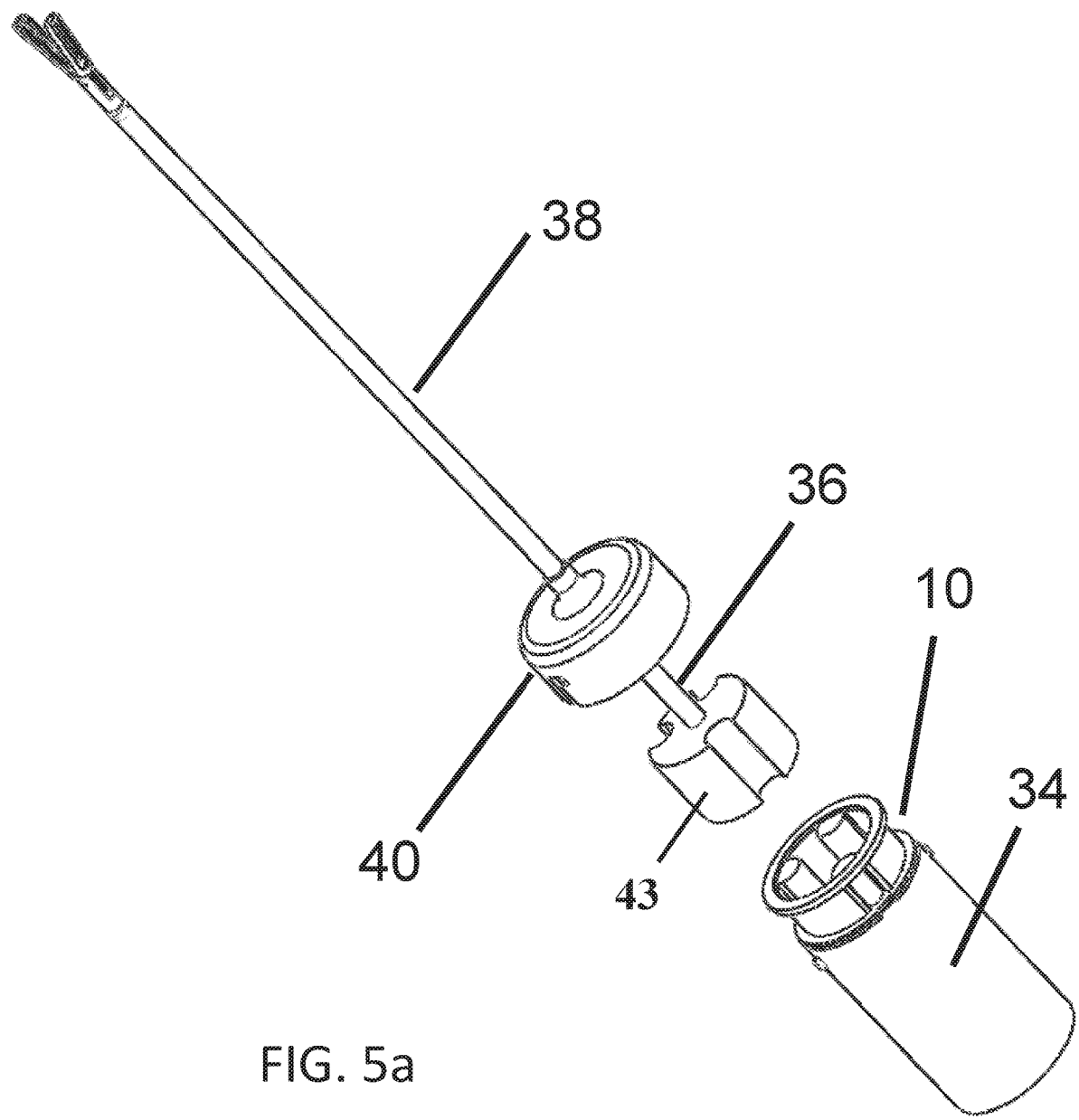
FIGS. 5a-c illustrate coupling of a tool shaft to the adaptor mounted on the drive mechanism.

As is shown in FIG. 5a, surgical tool 36 includes a gear mechanism 43 for translating the movement of the handle drive mechanism to movement of shaft 38 and a surgical device (e.g. grasper) connected thereto. Gear mechanism is described in greater detail below with reference to FIG. 5d.

Figure 5B:
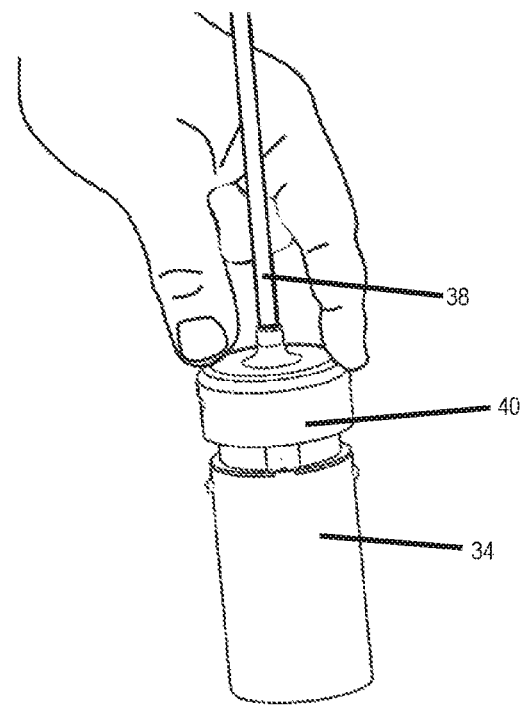
Figure 5C:
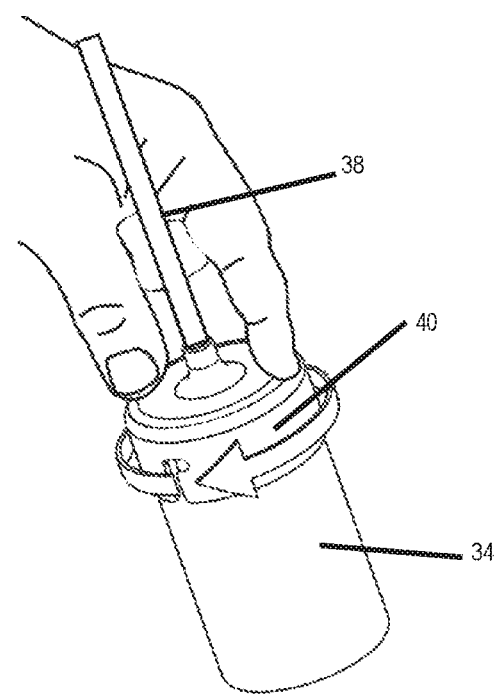

When adaptor 10 is collapsed (closed) and secured as shown in FIGS. 5b-c, the handle drive mechanism (drive shaft) engages gear mechanism 43 of surgical tool 36 through holes 32 in adaptor 10 and housing of gear mechanism 43. Although the potentially contaminated drive mechanism of the handle will contact a sterile shaft portion, this portion of the shaft will be sequestered within adaptor 10 and thus while the surgical procedure it would not be exposed to the operator (surgeon) or environment. To disengage shaft 38 from handle drive mechanism (and handle), cap 40 is rotated in the direction opposite to closure.

When cap 40 is opened, segment 14 and 16 are telescopically forced apart keeping gear mechanism 43 away from any contaminated portions of the handle drive mechanism while still being protected within adaptor 10.

Figure 5D:
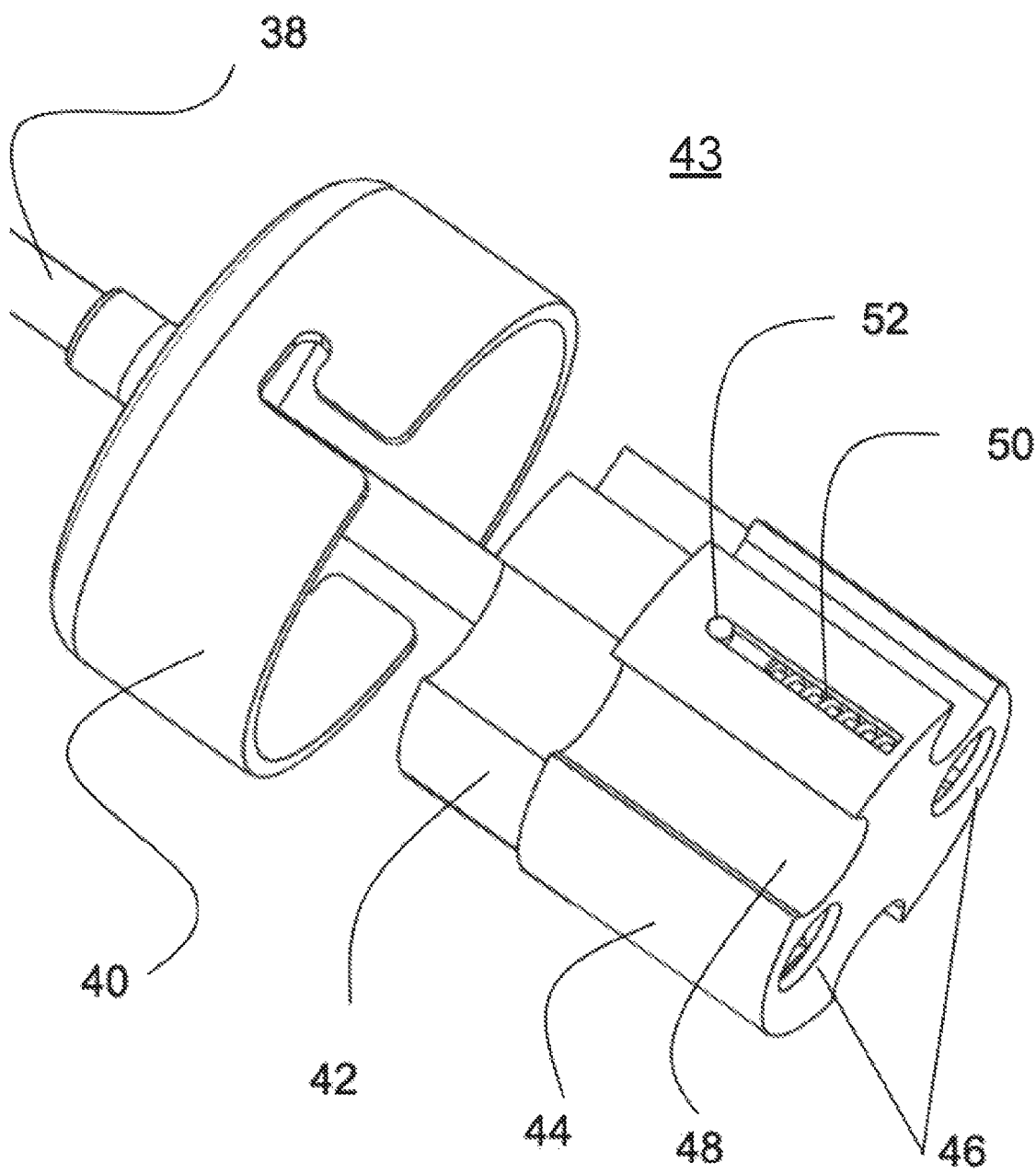
FIG. 5d illustrates the gear housing of the surgical tool.

FIG. 5*d* illustrates gear housing 43 which is formed from collapsible portions 42 and 44. Portion 42 translates the rotation of the motors (within handle) to the movements of shaft 38 and shaft tip (and tool). Portion 44 of the housing slides within portion 42. One or more springs 50 (one shown) compresses when housing 43 is telescopically collapsed by pushing portion 44 into portion 42. The tension in spring 50 allows telescopic expansion of housing 43 when a locking mechanism is released. Segment 44 also includes rods recess fitted with pins 24 for guiding telescopic movement of portions 42 and 44. Spring(s) 50 and rods 22 fit into holes (not shown) in portion 44. Pins 24 fit into guide groove in portion 44. To couple the tool to the drive mechanism of the handle, a user fits portion 44 of housing 43 into segment 14 of adapter 10 connected to the handle.

When coupled portion 44 enable the drive mechanism (drive shaft) to engage the proximal portion of shaft 38 of the surgical tool through holes 32 (FIG. 3) of adapter 10 and through holes 46 of portion 44 of housing 43.

When portion 44 is disengaged from segment 14 of adapter 10, it is telescopically extended out (by spring(s) 50) maintaining portion 44 away from potentially contaminated inner regions of portion 42. Thus, the region of shaft 38 exposed to the drive mechanism is protected by adaptor 10 while shaft 38 is protected by segment 44.

Housing 43 of the surgical tool can include electronic circuitry (or chip) that may be activated when the surgical tool is engaged with the handle drive. The activation may be triggered by direct contact or wirelessly. Data stored on the circuit/chip may be used for authentication of the surgical tool and its manufacturer, and for counting the number of procedures the tool was used in and/or the amount of time the tool or any of its components were used.

Additional data can refer to tool parameters of activation such as range of movement, maximal current on each motor, maximal current on entire device, speed of movement etc.

The circuit/chip can also store information relating to the position of each motor when the tool was disengaged from the handle. This allows the surgeon to change tools without the need of any calibration or the need to reset the tools to a 'home position' before engaging or disengaging the tool.

The present invention also encompasses use of two adaptors, one fitted to the handle and other fitted to the surgical tool for coupling the handle to the surgical tool.

Such a two adaptor system would render both device components coupled thereby functionally sterile even when disconnected from each other.

The user can couple the two adaptors via telescopic collapse and lock to operatively engage the handle with the tool. When disassembled, the potentially contaminated regions of both device components (handle and tool) remain covered by their respective (attached) adaptor. Thus, this adaptor system enables a user to use and store a device shaft or handle as if they were sterile thus allowing assembly and disassembly any number of times throughout a procedure.

The present invention also encompasses use of a tool shaft adaptor configured for use with adaptor 10 described hereinabove. FIGS. 6*a*-10 illustrate one embodiment of a shaft adaptor which is referred to herein as adaptor 100.

Adaptor 100 functions in protecting the tool shaft from exposure while being capable of coupling with an adaptor 10 attached to a handle as described above or functioning on its own.

Figures 6A, 6B:
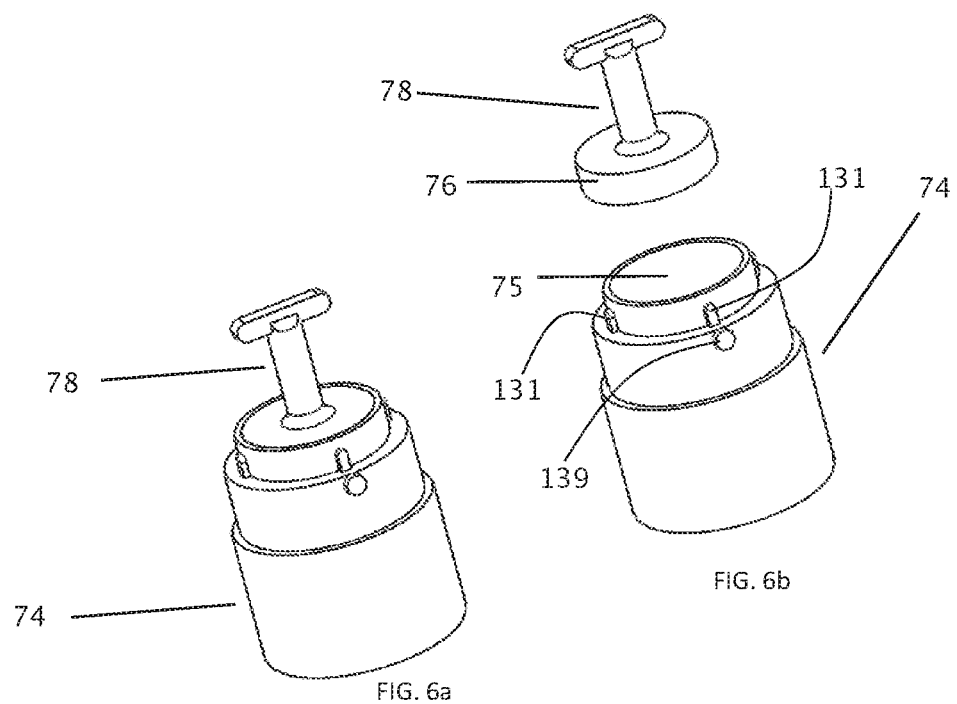

FIG. 6*a* illustrates a handle 74 adaptor fitted with cap 78 covering a top opening. This allows to use sterile processes such as autoclave or ETO without exposing sensitive parts like motors and electric circuits to potentially damaging environment and materials. FIG. 6*b* illustrates handle adaptor 74 with cap 78 removed ready to be coupled to a surgical tool.

Figure 7:
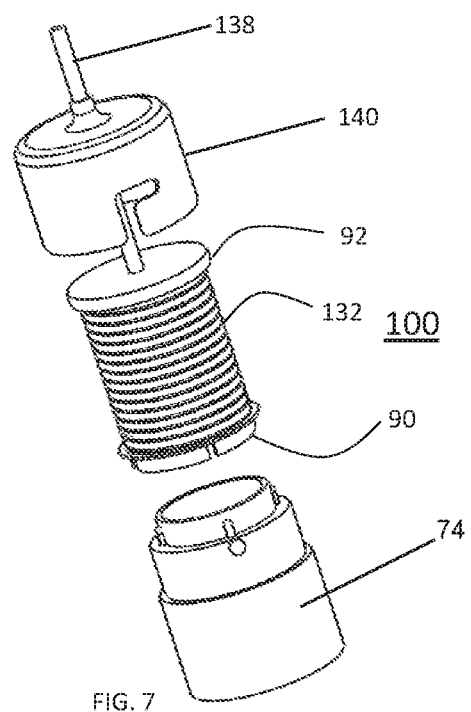

FIG. 7 shows the external parts of adapter 100, while the surgical tool is not connected to the drive handle, and flexible cover 132 is stretched out and covers the inner proximal parts, i.e. gear housing, of the surgical tool.

Adapter 100 enables coupling between a sterile surgical tool through the contaminated opening of a driving handle directly to the motors (or other parts such as electrical connectors) enabling the surgeon and the staff, to use the handle and the connected tool as a sterile unit. When adaptor 100 is disengaged both surgical tool and handle are protected from contamination and from contaminating the environment and surgical staff.

As is shown in FIG. 7, the three main parts of adaptor 100 are proximal ring 90 that is used as the connecting part of adapter 100 to the handle, a flexible sleeve 99 composed from spring 91 integrated into flexible envelope 98 and distal base 92 which serve as the roof of gear housing of the surgical tool (not shown in this figure).

FIG. 7 also shows cap 140 that secures the surgical tool to the handle.

Figure 8A:
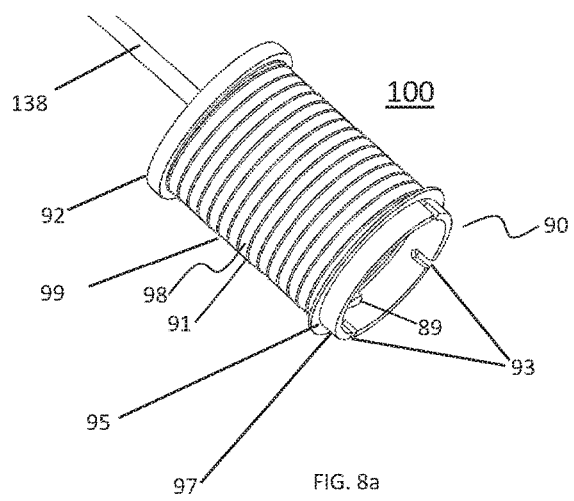
FIGS. 8a-c show in detail the sterile cover mechanism part of the surgical tool adaptor (FIGS. 8a-b) and underlying shaft connector (FIG. 8c).

FIG. 8*a* shows another view of adapter 100. Proximal ring 90 that serves as the connecting part to the handle has shoulder 95 that serves as a stopping ring that prevents the user from pushing the adapter further into the opening of the handle.

Figure 8B:
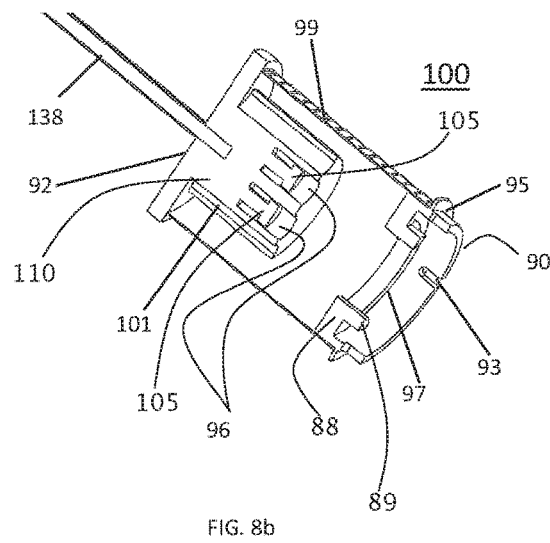
Figure 8C:
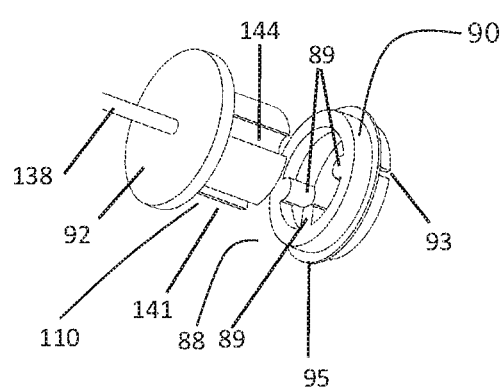

Adapting ring 97 has orienting grooves 93 for ensuring the right connection between adapter 100 and the drive handle opening. FIG. 8*b* is a cut away view of gear housing adopting ring 97 and its orienting rods 89. Also shown is gear housing 110 and connecting gear heads 105 located at openings 96. FIG. 8*c* shows adapter 100 with sleeve 99 removed to show proximal ring 90, housing 110 and the relation between these parts. Orienting rods 89 of ring 90 are shown and the grooves 144 and 141 of housing 110 that accept rods 89. Ring 90 is kept in the right orientation to the drive handle by using grooves 93 while keeping gear housing in the right orientation using orienting rods 89. The inner diameter of ring 90 is smaller than the inner diameter of the driving handle opening, preventing the gear housing from touching the potentially contaminated inner surface of the opening of the driving handle.

Figure 9:
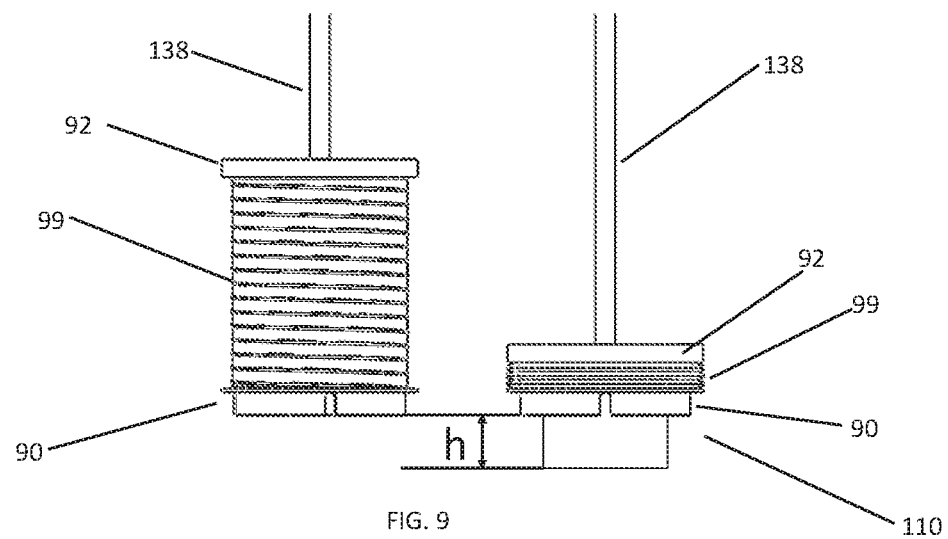

FIG. 9 shows the adapter in two states. The covering state (left image) where sleeve 99 is stretched out and covers housing 110 and eliminates contact therewith and the compressed state (right image) exposing housing 110 of the surgical tool allowing it to be engaged to the drive mechanism of the handle.

Figure 10:
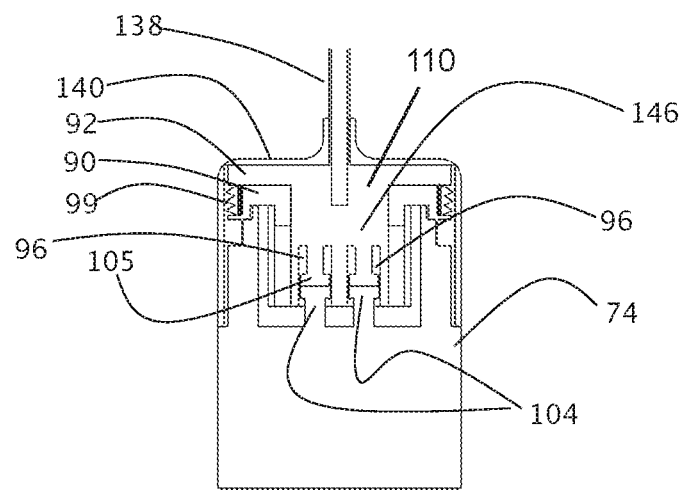

FIG. 10 is a cut view showing the assembled handle-adaptor system-surgical tool. Drive shaft 104 of handle 74 inserts into housing 110 via openings 96, and directly engages gears 105 of the surgical tool. Housing 110 does not touch the floor of nor the inner surface of the opening of handle 74. Sleeve 99 is contracted and hidden under cap 140 that secures the surgical tool to the handle.

The present invention also encompasses an adaptor for use with a handle. An embodiment of such a handle adaptor is shown in FIGS. 11*a*-*f* and is referred to herein as adaptor 210.

Figures 11A, 11B:
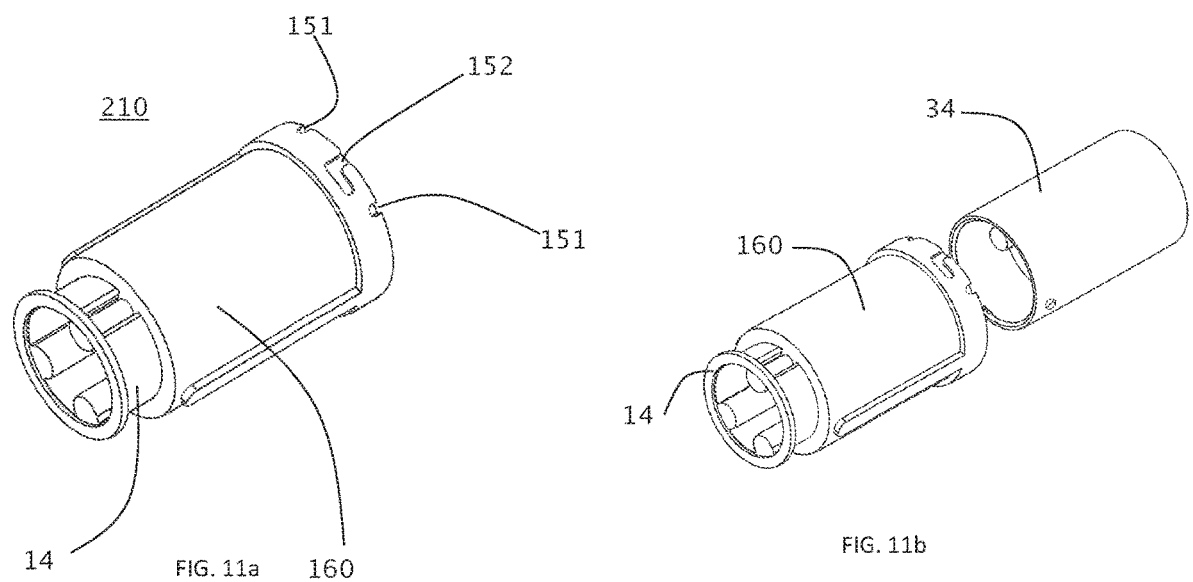
FIGS. 11a-e illustrate a handle adaptor constructed in accordance with the teachings of the present invention.

FIG. 11*a* is an isometric view of adaptor 210 showing the relationship between segments 14 and 160. Segment 14 includes one or more springs for enabling telescopic compression of segment 14 into segment 160 against a spring force. The spring(s) facilitate automatic telescopic expansion of adaptor 210 when released from the compressed state.

As shown FIG. 11b adapter 160 is designed as sealed compartment around a handle drive mechanism 34 (also referred to as drive mechanism 34).

When drive mechanism 34 is coupled to adaptor 210, pins in segment 160 maintain a correct orientation between segment 160 and handle drive 34.

Figure 11C:
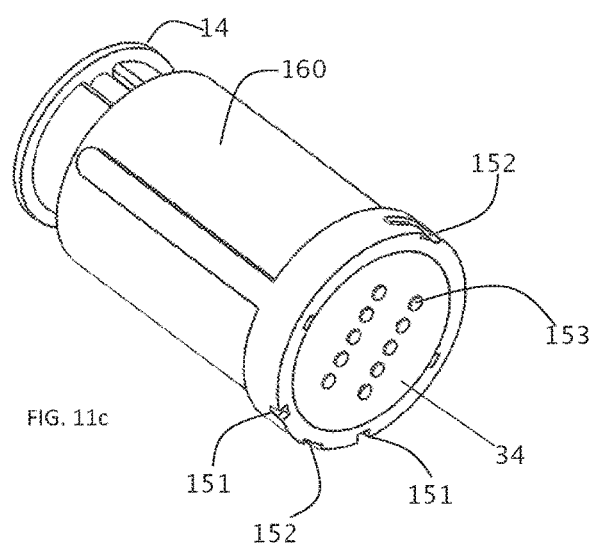

As shown FIG. 11c, the inner walls of segment 160 include orienting groove 151 and locking groove 152. These grooves will enable drive mechanism 34 to lock and seal within segment 160. Drive mechanism 34 may contain electrical or mechanical connectors 153. When locking drive mechanism 34 in segment 160, connectors 153 enable drive mechanism 34 (and an attached handle interface) to control a surgical tool connected to adaptor 210.

Figure 11D:
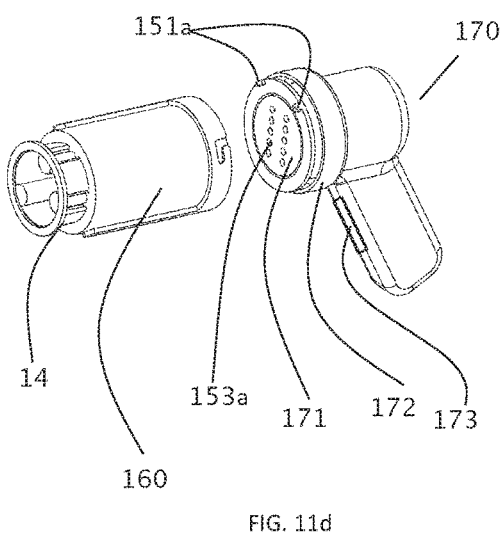

FIG. 11d, illustrate handle 170 (which carries drive mechanism 34) prior to coupling to adaptor 210. Recesses 151a are used for orienting handle 170 with respect to segment 160. Locking ring 171 uses groove 152 at of segment 160 to secure handle 170 to adaptor 210. When handle 170 and segment 160 are coupled, electrical connectors 153 and 153a contact allowing control over drive mechanism 34. The user controls the device via electrical switches 173 or mechanical actuators (not shown).

Figure 11E:
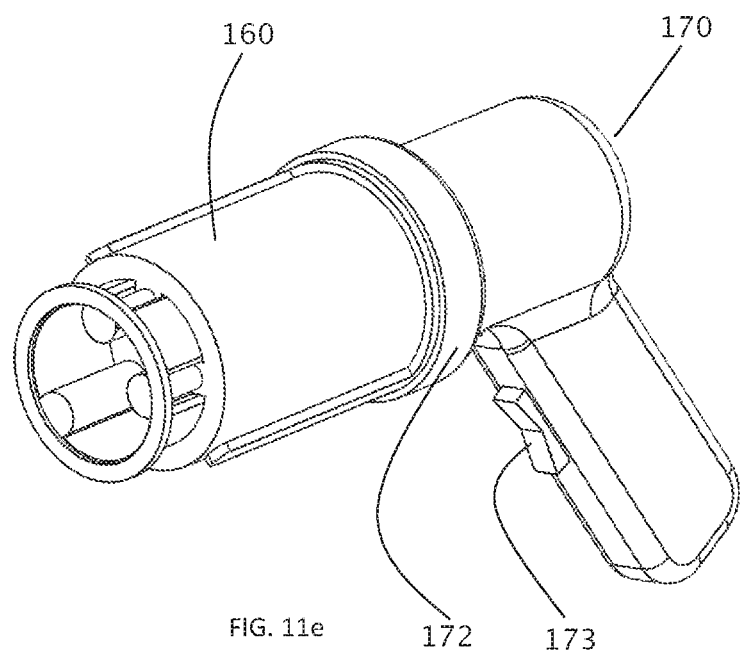

FIG. 11e illustrates handle 170 engaged to segment 160 of adaptor 210.

Figure 11F:
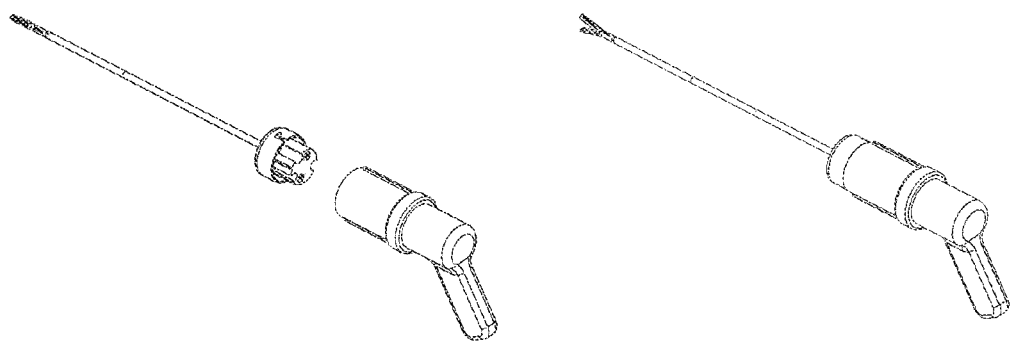
FIG. 11f illustrates the adaptor of FIGS. 11a-d attached to the handle (left) and coupled to the surgical tool (right).

FIG. 11f illustrates handle 170 and adaptor 210 prior to coupling to the surgical tool (left image) and following coupling to the surgical tool (right image).

Segments 14 and 160 of adaptor 210 include circumferential protrusions 28 and 30 (respectively). Protrusion 28 locks segment 16 to the opening of the electromechanical device to ensure that segment 16 will not move with respect to the covered non-sterile region. Protrusion 30 ensures the correct orientation between segments 14 and 160 to ensure that protrusion 28 will be at the right locking position.

As used herein the term "about" refers to ±10%.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. An adaptor for sterile isolation of a drive unit, the adaptor comprising two connectable segments, a first segment being engageable with the surgical tool and a second segment engageable with a motor drive shaft of the drive unit, wherein connecting said first and said second segments enables said motor drive shaft of the drive unit attached to said second segment to operate said surgical tool attached to said first segment while isolating said drive shaft of the drive unit from contaminates.

2. The adaptor of claim 1, wherein said first segment includes a first mechanism for engaging a shaft of said surgical tool.

3. The adaptor of claim 1, wherein said second segment includes a second mechanism for engaging said motor of the drive unit.

4. The adaptor of claim 3, wherein said first mechanism and said second mechanism operatively engage when said first and said second segments are connected.

5. The adaptor of claim 4, wherein said operative engagement is through gears.

6. The adaptor of claim 1, wherein said first segment and/or said second segment are configured so as to cover a potentially contaminable region of the drive unit.

* * * * *